(12) United States Patent
Freitag et al.

(10) Patent No.: US 7,238,538 B2
(45) Date of Patent: Jul. 3, 2007

(54) CHROMATOGRAPHIC ASSAY DEVICE AND METHODS

(76) Inventors: Helmut E. Freitag, Chemnitzstrasse 13, Schleswig 24837 (DE); Qinwei Shi, 55 Hearthstone Crescent, Richmond Hill, Ontario (CA) L4B 3E3

( * ) Notice: Subject to any disclaimer, the term of this patent is extended or adjusted under 35 U.S.C. 154(b) by 143 days.

(21) Appl. No.: 10/711,408

(22) Filed: Sep. 16, 2004

(65) Prior Publication Data

US 2005/0244985 A1    Nov. 3, 2005

Related U.S. Application Data

(60) Provisional application No. 60/504,540, filed on Sep. 19, 2003.

(51) Int. Cl.
*G01N 33/558*    (2006.01)

(52) U.S. Cl. .......................... 436/514; 422/56; 422/57; 422/58; 422/61; 435/287.1; 435/287.2; 435/287.7; 435/287.9; 435/805; 435/810; 435/970; 435/975; 436/65; 436/510; 436/518; 436/525; 436/810; 436/814; 436/818

(58) Field of Classification Search ............... 422/56, 422/57, 58, 61; 435/287.1, 287.2, 287.7, 435/287.9, 805, 810, 970, 975; 436/65, 510, 436/514, 518, 525, 810, 814, 818

See application file for complete search history.

(56) References Cited

U.S. PATENT DOCUMENTS

| | | | |
|---|---|---|---|
| 4,094,647 A | 6/1978 | Deutsch et al. | |
| 4,235,601 A | 11/1980 | Deutsch et al. | |
| 4,361,537 A | 11/1982 | Deutsch et al. | |
| 4,444,879 A * | 4/1984 | Foster et al. | 435/7.95 |
| 5,120,643 A | 6/1992 | Ching et al. | |
| 5,468,648 A | 11/1995 | Chandler | |
| 5,622,871 A | 4/1997 | May et al. | |
| 5,648,274 A | 7/1997 | Chandler | |
| 5,726,010 A * | 3/1998 | Clark | 435/5 |
| 5,807,863 A | 9/1998 | Eberle et al. | |
| 5,848,838 A | 12/1998 | Presta | |
| 5,856,503 A | 1/1999 | Aebi et al. | |
| 5,869,345 A | 2/1999 | Chandler | |
| 5,877,028 A | 3/1999 | Chandler et al. | |
| 5,998,220 A | 12/1999 | Chandler | |
| 6,017,767 A | 1/2000 | Chandler | |

(Continued)

FOREIGN PATENT DOCUMENTS

WO    WO8808534 A1 *    11/1988

*Primary Examiner*—Christopher L. Chin
(74) *Attorney, Agent, or Firm*—Sim & McBurney; Lola A. Bartoszwic

(57) ABSTRACT

A chromatographic assay device for the analysis of an analyte in a liquid sample has a proximal sample application zone and a distal test zone. The test zone contains a first ligand capable of binding with the analyte to form an analyte-ligand complex. The device also includes a spatially distinct reservoir containing a labeled reagent capable of binding to the analyte-ligand complex; an absorbent sink which is positioned to be capable of drawing the contents of the spatially distinct reservoir through the test zone; and structures for contacting the spatially distinct reservoir with the chromatographic medium so that the labeled reagent migrates from the reservoir to the absorbent sink, and thereby through the test zone to determine the presence or absence of the analyte. The device is used in a method for detecting analyte.

27 Claims, 4 Drawing Sheets

U.S. PATENT DOCUMENTS

| | | |
|---|---|---|
| 6,168,956 B1 | 1/2001 | Chandler |
| 6,187,598 B1 | 2/2001 | May et al. |
| 6,228,660 B1 | 5/2001 | May et al. |
| 6,528,321 B1 | 3/2003 | Fitzgerald et al. |
| 6,534,320 B2 | 3/2003 | Ching et al. |

* cited by examiner

CHROMATOGRAPHIC ASSAY DEVICE AND METHODS

CROSS-REFERENCE TO RELATED APPLICATIONS

This application claims the benefit of U.S. Provisional Application 60/504,540 filed Sep. 19, 2003. The entire contents of the prior application are hereby incorporated by reference.

FIELD OF THE INVENTION

The present invention relates to improved chromatographic assay devices, and particularly to those assay devices used to conduct immunological and serological binding assays. The invention relates to improved capillary flow devices which can be used to detect qualitatively or quantitatively the presence or absence of analytes of interest in biological samples, although it is not so limited. The invention also relates to methods of using such devices.

BACKGROUND OF THE INVENTION

Binding assays are in wide use in laboratories for the detection and measurement of analytes in samples. For biological samples such as urine, whole blood, plasma, serum, and other biological fluids, assays are often performed in hospitals and clinical laboratories. Binding assays can also be performed in environmental, agricultural, veterinary, industrial, athletic, and legal/forensic settings. The principles involved in such assays are well known by those skilled in the art. Many such devices have been described and are available commercially.

For convenience and to facilitate description and understanding of the novel devices of this invention, it will principally be described as applied to immunological assays in which the analyte is an antigen, the detection reagent is a labeled antibody, and the capture molecule is another antibody. The skilled artisan will recognize that the principles and practices described can be usefully employed to analyze a wide variety of analytes, including:

Oncology antigens. Certain antigenic compounds from human subjects are found in abnormal quantities or abnormal locations in the body. For example, the presence of elevated levels of antigens such as prostate specific antigen (PSA) and carcinoembryonic antigen (CEA) can be early indicators of tumorigenic processes.

Other antigens. Certain other naturally occurring antigens in the body can be indicative of disease processes. For example, the presence of human hemoglobin in human fecal occult blood samples can be indicative of gastrointestinal disorders.

Hormones. Human chorionic gonadotropin (hCG) is frequently assayed as a test for pregnancy.

Antigenic determinants of infectious disease organisms, including bacteria, fungi, viruses, and yeast. Common assays include assays for antigens known to be associated with infection by hepatitis, HIV, human papillomavirus (HPV), malaria, West Nile Virus, *Mycobacterium tuberculosis*, and *Helicobacter pylori*.

Antibodies raised by the immune system against antigens found on infectious disease organisms. Common assays include assays for antibodies against the hepatitis group of viruses, HPV, HIV, *Helicobacter pylori*, and malaria.

Drugs and metabolites thereof. Assays have been used to monitor the therapeutic efficacy of the drug. Assays can also be used to assess illegal usage of legal drugs, for example in the athletic context, as well as usage of illegal drugs.

Vitamins and metabolites thereof.

Enzymes. The absence or diminished quantities of certain enzymes can be diagnostically important in the inherited metabolic diseases, for example histidase as a marker of histidinemia, and hexosaminidase as a marker of Tay-Sachs disease.

Tissue specific antigens. The presence or elevated level of a tissue specific antigen in circulation may often be an indication of tissue damage. For example, cardiac troponin is a marker of myocardial infarction, and creatine kinase is a marker of muscle damage.

There are a few common types of immunological binding assay formats, such as described in Ching et al, U.S. Pat. No. 5,120,643, the contents of which are incorporated herein by reference. The first are competitive binding assays, which can be used to determine the concentration of an analyte in a sample solution. In competitive binding assays, known quantities of labeled reagents and unlabeled analytes for example labeled and unlabeled antigens or antibodies compete for binding sites on an immobilized binding material. After an incubation period, unbound materials are washed away from the system, and a measurement is made of the amount of labeled reagent bound to the binding material. The measurement is made by comparing the amount of binding to one or more known reference standards. In this way, the concentration of the analyte in the sample may be determined.

A second type of immunological binding assay is the sandwich assay. This assay format typically involves a porous media having a mobilizable labeled antibody and an immobilized unlabeled antibody partner for the analyte of interest in the biological sample. These antibodies are often referred to as the conjugate or detection antibody and the capture antibody. The sample is added to the porous media, to allow for formation of labeled mobilizable product which moves along the porous media to contact and react with the capture antibody to form a fixed, detectable, concentrated capture antibody/analyte/detection reagent complex. Sandwich assays may include immunological assays wherein the labeled reagent and the second binding partner are both antibodies, or are both antigens, and may also include other types of molecules. For example, enzyme immunoassays (EIA) and enzyme-linked immunosorbent assays (ELISA) are types of sandwich immunoassays, in which the binding is between an antibody and an antigen, and the labeling partner is an enzyme.

Many of these binding assays can be conducted in liquid phase or in modified liquid phase by applying liquids to a solid substrate—i.e. test tubes, microtiter plates or other similar bulk formats in which reagents are added sequentially and directly by a laboratorian. However, in clinical laboratories the use of solid phase chromatographic binding assay devices has become commonplace for their relative ease of use, economy, and reproducibility.

Typically, these chromatographic assay devices are comprised of a porous chromatographic medium which acts as the matrix for the binding assay. The sample of interest is added directly or indirectly to one end of the medium, and is chromatographically transported to a detection reagent with which it reacts to form a labeled product, which is then transported to a test zone containing an immobilized capture reagent such as a capture antibody, in which the presence, absence, or quantity of an analyte of interest can be determined.

For example, Deutsch et al. (U.S. Pat. Nos. 4,094,647; 4,235,601; and 4,361,537), the contents of which are incorporated herein by reference, describe binding assays where detection and capture reagents are deposited on a test strip with appropriate spacing in between them. Upon application of the sample, the reagents react and the product is transported to the test zones by chromatographic solvent transport. The Deutsch et al. devices include a retarding agent which slows transport of either the analyte of interest or of a product including the analyte of interest.

Ching et al. (U.S. Pat. Nos. 5,120,643 and 6,534,320), the contents of which are incorporated herein by reference, describe a test strip assay device in which a mobile conjugate labeled with colloidal labels such as gold, can be deposited on a chromatographic medium, and after reaction with an analyte, thus transported with the solvent to a test zone. Ching et al. describe a zone containing a dried conjugate. The conjugate/reagent product is solubilized by the movement of the sample down the strip toward the test zone. In some embodiments of the Ching et al device, the labeled reagent can be deposited on the test strip downstream of the test zone, and in others it can be premixed with the sample prior to its application onto the strip.

Ching et al. also teach the use of chromatographic transport "facilitating agents" which are stated to promote chromatographic transport, and to prevent aggregation and inactivation of specific binding materials and reagents in solution. The facilitating agents include polyethylene glycol, meta-soluble proteins such as casein, and detergents such as SDS.

May et al. (U.S. Pat. Nos. 5,622,871; 5,656,503; 6,187,598; and 6,228,660), the contents of which are incorporated herein by reference, describe a home pregnancy test in which the labeled mobilizable detection reagent reacts with an analyte and the resulting product migrates with the liquid sample as the sample progresses to the test zone. During manufacture, after the unlabeled binding agent (an anti-hCG antibody) is added to and immobilized in the test zone, the remainder of the test strip material is treated with blocking agents, in order to block any remaining binding sites. Suitable blocking agents are described as protein and polyvinylalcohol. Additional manufacturing steps include the addition of a glaze of aqueous sugar or cellulose solution onto the test strip in the region where the labeled capture reagent will be deposited. May et al. hypothesize that the glazing prevents interaction between the detection reagent and the test strip. After the glazing step, the detection reagent is deposited on the test strip.

Chandler et al. (U.S. Pat. Nos. 6,168,956; 6,017,767; 5,998,220; 5,877,028; 5,869,345; 5,846,838; 5,648,274; 5,607,863; 5,468,648; and 6,528,321), the contents of which are incorporated herein by reference, describes an assay device with opposable elements in a flexible or hinged book structure. For example, U.S. Pat. No. 5,846,838 describes a device in which a first opposable element contains a sample preparation zone, and in which the second opposable element contains the chromatographic medium. Chandler et al. describe bringing the two opposable portions of the test into contact with each other functions to apply the sample to the chromatographic medium, thereby starting the test. Chandler et al. use the first opposable element to bring certain reagents into contact with the chromatographic medium. The Chandler devices describe movement of the sample through the test zone of the chromatographic medium at the same time as the labeled reagent.

Fitzgerald et al. (U.S. Pat. No. 6,528,321), the contents of which are incorporated herein by reference, describe a chromatographic device having two opposable elements. The first element contains a sample application zone which consists of a porous matrix material capable of trapping the cellular components of blood; and a chromatographic medium comprising a test zone with a specific binding partner for the analyte of interest and further comprising a detection reagent zone with a labeled second specific binding partner for the analyte, which can be resolubilized by the solvent front passing through the porous material. The second opposable element contains an applicator and an absorber. When the two opposable elements are brought into contact with each other by the operator, the applicator releases a wash solution onto the first opposable element. The Fitzgerald et al. device, like the Ching et al. device, provides that the labeled reagent flow through at least a portion of the chromatographic medium contemporaneously with the sample.

A careful analysis of the patents listed above reveals that except for the Chandler devices, a principal feature is that they employ lateral flow of the samples which are usually in the same planes through a detection zone and a capture zone which are in substantially the same plane. Another feature is that the analyte in the sample first migrates to a detection zone where the analyte reacts with a labeled detection reagent and the resulting product then migrates to the test zone to form and concentrate a detectable complex. The hinged devices are somewhat different from the standard structures in that the reactants are not in a lateral line. They are initially in parallel planes in the two components. The components are brought into opposition to permit the detection reagent/ analyte product to react with a capture reagent to form the detectable complex. In all structures the first reaction is between the analyte and the detection reagent in approximately the same or parallel planes and the resulting detection reagent/analyte product thereafter contacts and reacts with the capture reagent to form a detectable complex.

Currently available chromatographic assay devices such as described in the above patents suffer from some drawbacks and limitations. Most commercially available porous membranes have some innate capacity for non-specific binding. Many of the prior art assay devices utilize extrinsic blocking agents to minimize non-specific binding of the labeled reagent to the test strip. Non-specific binding between labeled reagent and the test strip can lower the sensitivity and reproducibility of the test, and can also create an undesirable background of labeled reagent which renders reading a color reaction more difficult. Blocking agents can also cause viscosity increases, which can change the flow characteristics of the test strip.

Moreover, in many of the prior art devices the labeled detection reagent is transported to the test zone at the solvent front. As a result, these prior art assay devices may exhibit uneven color banding or streaking due to the variable flow rate and characteristics at the solvent front, where the elution of the labeled reagent can be uneven. The streaking or color banding is undesirable as it can increase background, and can render reading a result difficult, due to uneven labeling in the test zone, and also due to the appearance of faintly positive weak test lines which can be difficult to interpret.

In some prior art test devices, particularly those used for EIAs and ELISAs, liquid carriers such as water, buffers and the like must be added to the test strip or to the sample during the test operation, which increases the possibility of operator error, and increases the complexity of the test operation. Moreover, elimination of reagents such as blocking agents, glazing agents, and facilitating agents during the manufacturing process may provide improved assay sensitivity, reproducibility and reliability, and overall a more efficient and economical assay production.

SUMMARY OF THE INVENTION

The present invention provides a chromatographic assay device for the analysis of an analyte in a liquid sample. The device comprises a chromatographic medium having a proximal sample application zone and a distal test zone, in which the test zone contains a first ligand capable of binding with the analyte to form an analyte-ligand complex;
  a spatially distinct reservoir containing a labeled reagent capable of binding to the analyte-ligand complex;
  an absorbent sink which is positioned to be capable of drawing the contents of the spatially distinct reservoir through the test zone; and
  means for contacting the spatially distinct reservoir with the chromatographic medium so that the labeled reagent migrates from the reservoir to the absorbent sink, and thereby through the test zone to determine the presence or absence of the analyte.

The invention also provides a method for determining the presence, absence or quantity of at least one analyte in a liquid sample comprising the steps of:
  a) providing an assay device comprising a housing which contains
  a first component which is a chromatographic test strip through which the sample flows by capillary action from a sample application zone to contact a downstream test zone on the test strip, said downstream test zone containing an unlabelled immobile first reactant which reacts with the analyte if present to form an unlabelled reactant/analyte product;
  a second component separated from the first component and carrying a second, mobilizable, labeled reactant which is so placed on as to be moved into contact with the unlabelled reactant/analyte product to form a detectable unlabelled reactant/analyte/labeled reactant complex;
  said first reactant and said second reactant being initially separate but in a spatial relationship such that they can be brought together after formation of the unlabelled reactant/analyte product to permit the reaction which forms the detectable unlabelled reactant/analyte/unlabelled reactant complex;
  b) contacting the sample application zone with the liquid sample such that the analyte moves to the test zone by capillary action to form a reaction product;
  c) contacting the labeled reagent with the reaction product to form a detectable reaction complex.

BRIEF DESCRIPTION OF THE DRAWINGS

Other features, aspects and advantages of the invention will be better understood by reference to the following drawings in which.

DETAILED DESCRIPTION OF THE INVENTION

Figure 1:
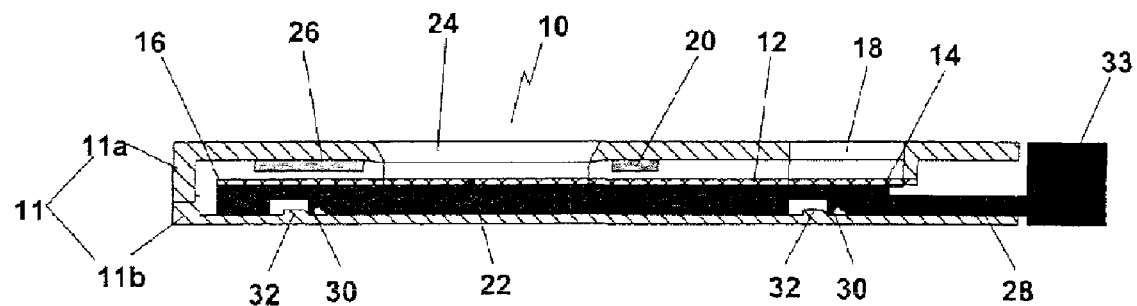
FIG. 1 is a cross-sectional elevation of one embodiment of an assay device of the present invention.

It is an object of the present invention to provide improved chromatographic assay devices which alleviate some of the problems of the prior art devices. In particular, the devices of the present invention provide a chromatographic test strip for detecting the presence, absence or quantity of an analyte of interest in a liquid sample. As a first step, the liquid sample is added to the test strip, and moved by capillarity across a test zone containing an immobilized ligand which is a capture molecule. Thus, the test strip is wetted with sample prior to the final detection of the analyte. A labeled detection reagent which detects the presence of the analyte is provided with the test strip, stored in a resolubilizable form. In a second step, the dry labeled reagent and an absorbent sink are brought into contact with the wetted test strip, thereby resolubilizing the reagent, and drawing it through the test zone by the forces of capillary action.

For example, if the analyte is an antigenic marker of a cardiac event such as myoglobin, the capture molecule could be a first antibody to myoglobin and the detection reagent a labeled second antibody to myoglobin. The first antibody is fixed and unlabeled. It forms with the myoglobin a fixed reaction product. After the fixed reaction product forms, the second, mobile, detection antibody is moved into a position where it will be able to contact and react with the fixed reaction product to form a fixed, detectable, unlabeled antibody/myoglobin/labeled antibody complex.

According to the present invention, the labeled detection reagent moves into the test zone after the test zone has been wetted with sample, and preferably after the entire strip has been wetted. The sample has moved through the test strip prior to the resolubilization of the labeled reagent. This pre-impregnation reduces non-specific binding between the labeled reagent and the test strip. A consequence of the present invention is that the analyte of interest is already enriched in the test zone, before coming into contact with the labeled detection reagent. As a result, a smaller amount of labeled reagent can be used to manufacture assays of comparable or increased sensitivity as compared to the prior art devices.

The present invention is particularly advantageous over the prior art devices to test for antibodies against infectious diseases (IgG or IgM) or allergens (IgE). Often, such antibodies are found in small concentrations in liquid samples, but the concentration of total IgG, IgM or IgE can be high. Where, as in the prior art devices, the labeled reagent travels through the chromatographic medium with the sample, it may bind to the total IgG, IgM, an IgE concentration, and thereby decrease test sensitivity. The present invention permits binding of the sample antibody with an immobilized capture molecule at the test zone. This step serves to enrich the analyte concentration at the test zone. After that enrichment, the labeled reagent is drawn through the test zone, providing a test of increased sensitivity, consuming less labeled reagent.

The present invention also provides advantages over the prior art devices in that many prior art devices use a monoclonal antibody as the detection reagent. Monoclonal antibodies are preferred over polyclonals in the prior art devices due to the tendency of polyclonal antibodies to bind at multiple or various binding sites on the same analyte, which decreases the efficiency of the labeled mobile reaction product for binding to the antibody to form a detectable complex. According to the present invention, the analyte is already captured and immobilized in the test zone prior to contact and reaction with a labeled reagent to form a detectable complex.

Since certain terms are employed in the explanation of the principles and practice of this invention, it will assist in the understanding thereof to define these terms at this juncture. Unless otherwise indicated, the following terms as used herein are defined as follows:

"Absorbent sink" as used herein refers to the unwetted portion of the chromatographic medium or a separate pad which is used to facilitate or induce movement by capillary action.

"Analyte" is the molecule whose presence, absence or quantity is to be detected. Analyte includes the actual molecule to be assayed, and also includes molecules that are analogs, fragments, precursors, intermediates, degradation products, reaction products, and derivatives thereof, provided that such molecules bind another molecule used in the assay in a manner substantially equivalent to that of the analyte itself. Analyte also includes complexes, aggregates and conjugates that contain the molecule to be detected.

"Capture molecule" is an unlabeled immobilized molecule which reacts with the analyte or its complex. It may, for example, be a second antibody to troponin, which binds to troponin/labeled troponin antibody complex.

"Detection reagent" is a labeled mobile or mobilizable molecule which binds to an analyte. It may, for example, in this invention, be a labeled troponin antibody which binds to troponin in a sample to form a mobile labeled antibody/analyte product.

"First component" as used herein refers to a chromatographic test strip containing at least one unlabeled reactant such as an unlabeled capture antibody and may contain an absorbent sink.

"Ligand" as used herein is any molecule that is capable of specifically binding to or reacting with an analyte of the present invention.

"Label" or "labeled" as used herein refers to any directly or indirectly detectable or determinable moiety that is covalently or non-covalently associated with a specific binding partner that binds one or more other specific binding partners in the performance of an assay utilizing an assay device of this invention. Labels suitable for use in the present invention are described in more detail below.

"Reagent" or "reactant" is a generic term which refers to any molecule which participates in the assay by a reaction or reactions which produce a detectable product. The meaning of the term will be readily understood in the descriptions and explanations in which it is employed.

"Reservoir" or "reagent reservoir" as used herein means a repository or supply of dried reagent such as a detection reagent. In some embodiments of the invention the reservoir is dried on to a structural member that is referred to herein as the "reservoir support". The characteristics of and materials used for the reservoir support are described in more detail below.

"Sample" as used herein refers to any specimen that can be applied to the assay device, directly or indirectly, and in unprocessed, processed, diluted, undiluted, or rehydrated liquid form, and that contains or may contain an analyte. "Sample" includes but is not limited to: specimens such as serum, plasma, whole blood, saliva, urine, cerebrospinal fluid, fecal extracts, stool, tissue samples, and swab material together with rehydrated forms of such specimens, forensic samples of the specimens described above; and agricultural or industrial specimens such as plant or animal material, sewage, waste water, effluents and the like.

"Second component" as used herein refers to that element of the test device which contains or supports a labeled, mobile reactant solubilizable in the liquid sample, such as a labeled myoglobin conjugate.

The principles, concepts and wide scope of this invention will be better understood by consideration of the herewith submitted figures which illustrate several preferred but non-limiting embodiments of the invention.

Turning to FIG. 1, one embodiment of a chromatographic assay device (10) according to the present invention is shown. The assay device includes a housing or casing (11) for the protection of the components of the device to achieve the desired results. The housing may be of integral construction, but in this embodiment is comprised of an upper portion (11a) and a lower portion (11b).

Contained within the housing (11) of the device is a test strip comprised of a porous chromatographic medium (12) which has a proximal (or upstream) end (14) and a distal (or downstream) end (16). The proximal end includes a sample application aperture (18) which permits the liquid sample for analysis to be applied directly or indirectly to a sample application zone (18a) on the chromatographic medium. A reservoir support (20) is positioned adjacent to, apart from and not in contact with the chromatographic medium. A reservoir of labeled reagent is dried on to the surface of the reservoir support facing the chromatographic medium. Test zone (22) is located on the chromatographic medium downstream of the reagent reservoir. The test zone can be monitored by the test operator through a viewing window (24) in the housing (11) of the assay device. An absorbent sink (26) is located downstream of the test zone, but spaced apart from the chromatographic medium. The absorbent sink (26) and the reservoir support (20) are adhesively affixed to the interior edge of the upper housing, so that they do not accidentally and prematurely contact the chromatographic medium. Alternatively, the absorbent sink and the reservoir may be affixed to the interior edge of the upper housing by mechanical means, or any other suitable means.

The chromatographic medium (12) is located upon a support structure (28). The lower face or surface of the support structure (28) contains pins (30) extending downward toward the lower portion of the outer housing. The chromatographic medium is in substantial contact with the support structure along the entire length of the chromatographic medium to provide mechanical support to the chromatographic medium.

The interior surface of the lower housing (11b) is equipped with ramped prongs (32) which provide a mechanism for the operator to bring the chromatographic medium (12) into contact with the absorbent sink (26) and the reagent reservoir on one surface of the reservoir support (20). The faces of the ramped prongs (32) are engageable with the pins (30) that are located on the interior edge of the support structure.

The support structure includes an actuating device (33) which enables the test operator to push the support structure toward the distal end of the assay device, which forces the pins (30) up the ramped face of the prongs of the lower housing, until the most distal end of the support structure (28) stops against the interior face of the distal edge of the housing, which in this embodiment is integral with the lower portion (11b) of the housing. Other stopping means are known to those of skill in the art. This actuation brings the support structure (and hence the chromatographic medium) upward and into contact with the absorbent sink (26) and the reservoir support (20).

Figure 2:
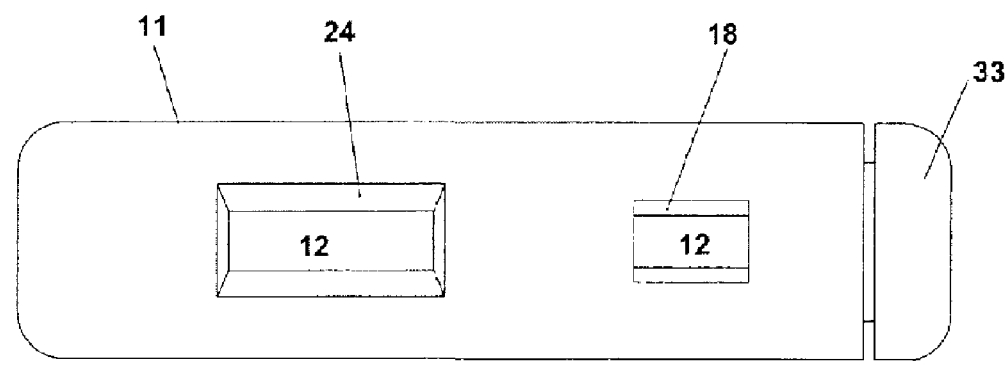
FIG. 2 is a top view of the assay device of FIG. 1.

FIG. 2 shows a top elevation of the device of FIG. 1, showing the housing (11), the viewing window (24), the sample application aperture (18), and the actuating device at the end of the solid support (33). The chromatographic medium (12) is visible through the sample application aperture and also through the viewing window.

In operation, an assay device of FIG. 1 and 2 is provided in which an unlabeled ligand such as an antibody is affixed to the chromatographic medium in the test zone. The unlabeled ligand is known to specifically bind to the analyte of interest, and acts as a capture molecule. The test operator applies a quantity of the biological sample suspected to contain the analyte of interest to the chromatographic medium through the sample application aperture (18) at the proximal end of the chromatographic medium. The sample is drawn downstream toward the distal end of the chromatographic medium by capillary action. If present, the analyte of interest will bind to the unlabeled immobilized ligand in the test zone, and the ligand-analyte bound pair will remain immobilized or fixed in the test zone. During this entire process, the reagent reservoir and the absorbent sink are retained spatially distinct and apart in a separate plane from the chromatographic medium.

Once the chromatographic medium is saturated with solvent, or after a predetermined period of time, but in any event once the operator can visualize that the test zone has been wetted with liquid, the operator contacts the reagent reservoir with the chromatographic medium by pushing the actuating device (33) of the support structure (28) toward the distal end of the device. The movement of the support structure brings the chromatographic medium up and into contact with the absorbent sink and the reagent reservoir. The absorbent sink draws further fluid toward the distal end of the chromatographic medium by capillary action. The placement of the reservoir of labeled detection reagent proximal to the test zone serves as a localized source of the labeled reagent to be drawn through the test zone toward the absorbent sink. Thus, in the test zone, the labeled reagent contacts the immobilized ligand-analyte product to which it will bind and form an immobilized complex which is detectable by the operator.

The assay device of FIGS. 1 and 2 may conveniently be used in an embodiment of the invention wherein the analyte of interest reacts with a capture molecule known to bind the analyte, and that analyte/capture product binds to the immobilized ligand in the test zone. For example, a capture molecule may be affixed to the test strip immediately downstream of the sample application zone. Addition of the sample to the test strip results in the analyte contacting the capture molecule (for example, a biotinylated antibody known to bind to the analyte), resulting in an analyte product having an attached capture molecule. That analyte complex proceeds through the test strip to the test zone, which contains an immobilized ligand known to bind to this particular analyte complex (in the example above, the immobilized ligand could be streptavidin, which is known to specifically bind to the capture biotin moiety in the analyte complex). As before, the operator then brings the reagent reservoir and the absorbent sink into contact with the wetted test strip, and the labeled reagent proceeds through the test zone to permit the operator to detect the analyte which, if present in the sample, has been immobilized in a detectable complex in the test zone.

The assay devices of FIGS. 1 and 2 may be employed in an immunological assay in which a bacterial antigen reacts initially with unlabeled fixed antibody to form a fixed product. The unlabeled antibody/analyte product is then brought into contact with a mobile, labeled antibody (a detection reagent) to form a labeled antibody/analyte complex which is detectable visually, or by other means.

Figure 3:
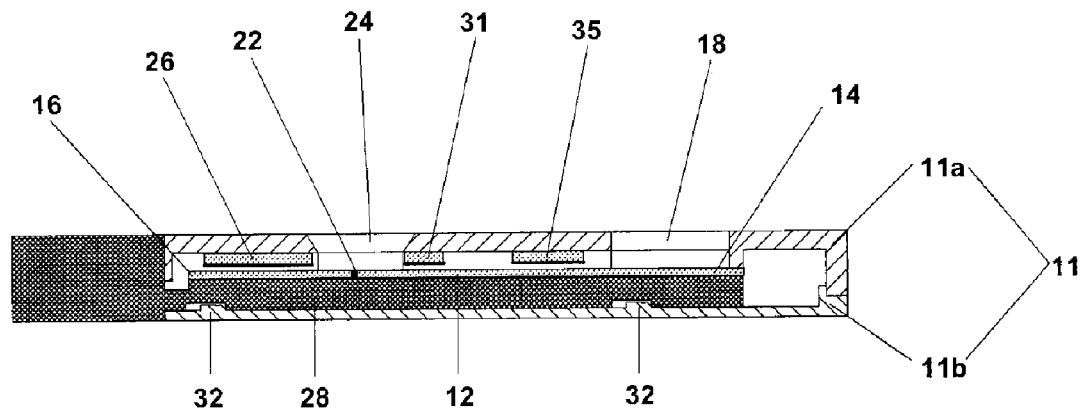
FIG. 3 is a cross-sectional elevation of a further embodiment of an assay device of the present invention.

FIG. 3 shows an embodiment of an assay device of the invention that can be used for an enzyme immunoassay (EIA). In the device of FIG. 3, the test strip of a chromatographic medium (12) has a proximal end (14) and a distal end (16). The housing (11) is comprised of an upper housing (11a) and a lower housing (11b). The upper housing includes a viewing window (24) and a sample application aperture (18) at or near the proximal end of the chromatographic medium. A distal test zone (22) is provided which can be monitored through the viewing window (24). The device in FIG. 3 also contains the chromatographic media (12), and a solid support structure (28) with a variation of the ramped prong and pin combination of the assay device of FIG. 1 and 2. In the device of FIG. 3, the actuating device (33) on the solid support is at the distal end of the device, rather than the proximal end. In this embodiment, the actuating device is pulled, rather than pushed, as a means of bringing the reagent reservoirs into contact with the chromatographic medium. Thus, the lower housing has ramped prongs (32), and the underside of the solid support (28) is correspondingly ramped to permit movement of the support relative to the housing so as to bring the chromatographic medium into communication with the reservoirs when the handle is pulled. The absorbent sink (26) is located distal to the test zone and spatially distinct from the chromatographic medium. The dimensions of absorbent sink (26) are selected so that it is not saturated until the labeled reagent has moved through the test zone. In the device of FIG. 3, there are two reservoir supports (31, 35) located between the sample application aperture (18) and the test zone (22). Each of the two reservoir supports is spatially apart from the chromatographic medium. In the device of FIG. 3, the reservoir support (31) which is closest to the test zone will contain a reagent that is to be carried through the test zone earlier than the reagent on reservoir support (35), which is farther from the test zone.

Figure 4:
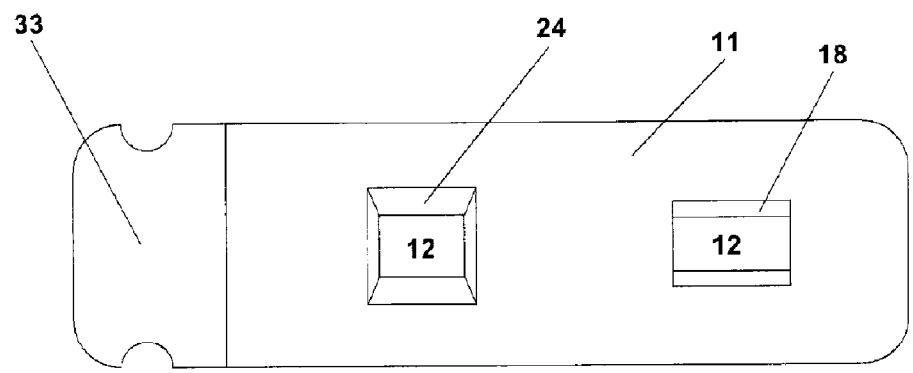
FIG. 4 is a top view of the assay device of FIG. 3.

FIG. 4 shows a top elevation of the device of FIG. 3, showing the housing (11), the viewing window (24), the sample application aperture (18), and the actuating device (33). The chromatographic medium (12) is visible through the sample application zone and also through the viewing window.

In operation, an assay device of FIGS. 3 and 4 is provided in which an unlabeled ligand (capture molecule) which is known to bind to the analyte of interest is immobilized on the chromatographic medium in the test zone. The test operator applies a quantity of the liquid sample suspected to contain the analyte of interest onto the chromatographic medium through the sample application aperture (18) at the proximal end of the chromatographic medium. The sample is drawn downstream along the chromatographic medium toward the distal end by capillary action. If present, the analyte of interest will bind to the unlabeled capture molecule in the test zone, and the resulting product will remain immobilized there. During this stage of the test, the reagent reservoirs and the absorbent sink are spatially distinct from the chromatographic medium.

Once the chromatographic medium is saturated with solvent, or after a predetermined period of time, but in any event once the operator knows that the test strip has been wetted with liquid, the operator contacts the contents of the reagent reservoirs with the chromatographic medium by pulling the handle of the support structure away from the distal end of the device. The movement of the support structure brings the chromatographic medium up and into contact with the absorbent sink and the reagent reservoirs. The absorbent sink draws further fluid distally along the chromatographic medium by capillary action. Reagent reservoir (31) which is located directly upstream of the test zone, contains an enzyme labeled reagent. Reagent reservoir (35) contains the enzyme substrate, for example, p-nitrophenylphosphate, and is positioned upstream of the reservoir containing the enzyme labeled reagent, for example, an alkaline-phosphatase conjugated antibody. Thus, although the contents of the two reagent reservoirs contact the test strip at approximately the same time, the location of the two reservoirs relative to each other and to the test zone enables ordered application of the reagents into the test zone as a function of the distance to the test zone and the flow rate of the particular reagents. Thus, in this embodiment of the invention, the enzyme-conjugated reagent will come into contact with the immobilized reagent-analyte product where it will bind and be immobilized. As time progresses and capillary action proceeds, the enzyme substrate will come into contact with the enzyme/ligand/analyte complex. The substrate will be acted upon by the enzyme, and thereby rendered detectable by the operator.

Instead of the two reservoirs (31, 35) illustrated in FIGS. 3 and 4 which contain the enzyme conjugated reagent and the enzyme substrate respectively, a similar device with an opposite configuration, in which actuating device is pulled instead of pushed can be prepared and used for testing.

Figure 5:
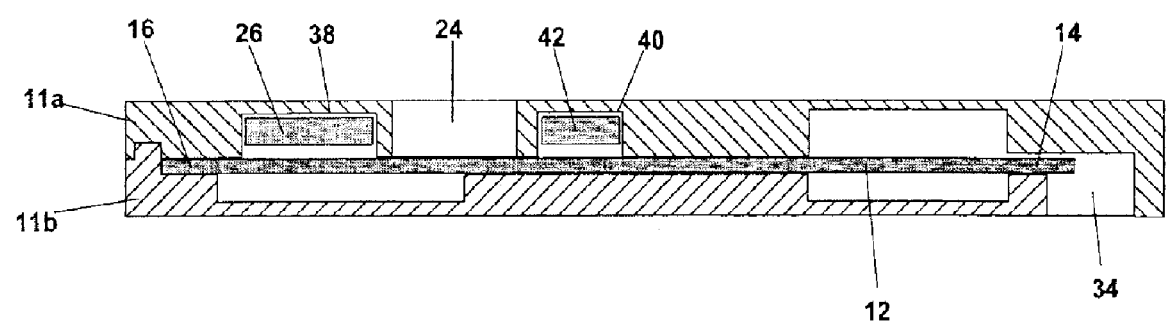
FIG. 5 is a cross-sectional elevation of a further embodiment of an assay device of the present invention.

FIG. 5 shows a further embodiment of an assay device of the present invention. The assay device of FIG. 5 is turned upside down during operation of the test, and so, for convenience "upper" and "lower" are relative to the illustration of FIG. 5, although it is understood that the positions of the housings relative to a fixed point, e.g. a countertop, may change during the operation of the test. In the device of FIG. 5, the chromatographic medium (12) has a proximal end (14) and a distal end (16). The chromatographic medium is affixed onto the interior surface of the lower housing (11b) in several places. The upper housing (11a) includes a viewing window (24) through which the test zone may be observed. The lower housing contains an aperture (34) which exposes a sample application zone at the proximal end of the chromatographic medium. The test strip is directly contactable through the aperture (34).

The upper housing of the device of FIG. 5 contains a recess (38) which is located upstream of the test zone, and which is adapted to receive a movable member of absorbent material (26) i.e. the absorbent sink. The upper housing also contains a second recess (40), intermediate between the sample application zone (34) and the test zone. The second recess (40) is adapted to receive a movable reservoir support (42) containing a quantity of labeled reagent on one surface to form a reagent reservoir. The labeled reagent is deposited onto the surface of the reservoir support (42) facing the chromatographic medium. The two moveable members are each slightly smaller than their respective recesses, so that when the device is turned with the sample application zone facing upward, gravity forces the moveable members down and away from the chromatographic medium. The shape and dimensions of the second recess (40) and of the reservoir support (42) are selected so that surface of the reservoir support containing the labeled reagent remains facing but apart from the chromatographic medium during transport or handling of the assay. Rotation or movement that brings an unlabeled surface of the reservoir support into contact with the chromatographic medium during operation is undesirable, as it can prevent satisfactory operation of the assay device. In the particular embodiment of the assay device that is shown in FIG. 5, there is no gap between the lower edge of the first and second recesses and the chromatographic medium. In some embodiments, such a gap may be included, but the dimensions of the gap and the moveable members should be sized such that the moveable members are restrained from moving beyond their respective recesses and along the test strip, which movement also can prevent satisfactory operation of the assay device.

The operator commences the assay by ensuring that the assay device is positioned so that the absorbent sink and the reagent reservoir are not in physical contact with the chromatographic medium, i.e. with the sample application window facing upwards. The operator then places a liquid sample onto the test strip in the sample application zone, so that the liquid is drawn downstream toward the distal end of the test strip by the forces of capillary action. Once the strip is fully wetted, the operator turns the assay device so that the viewing window is facing up. After this motion, gravity will bring the absorbent sink and the labeled reagent reservoir into contact with the wet chromatographic medium. The labeled detection reagent will be solubilized and then drawn through the test zone by capillary action.

Figure 6:
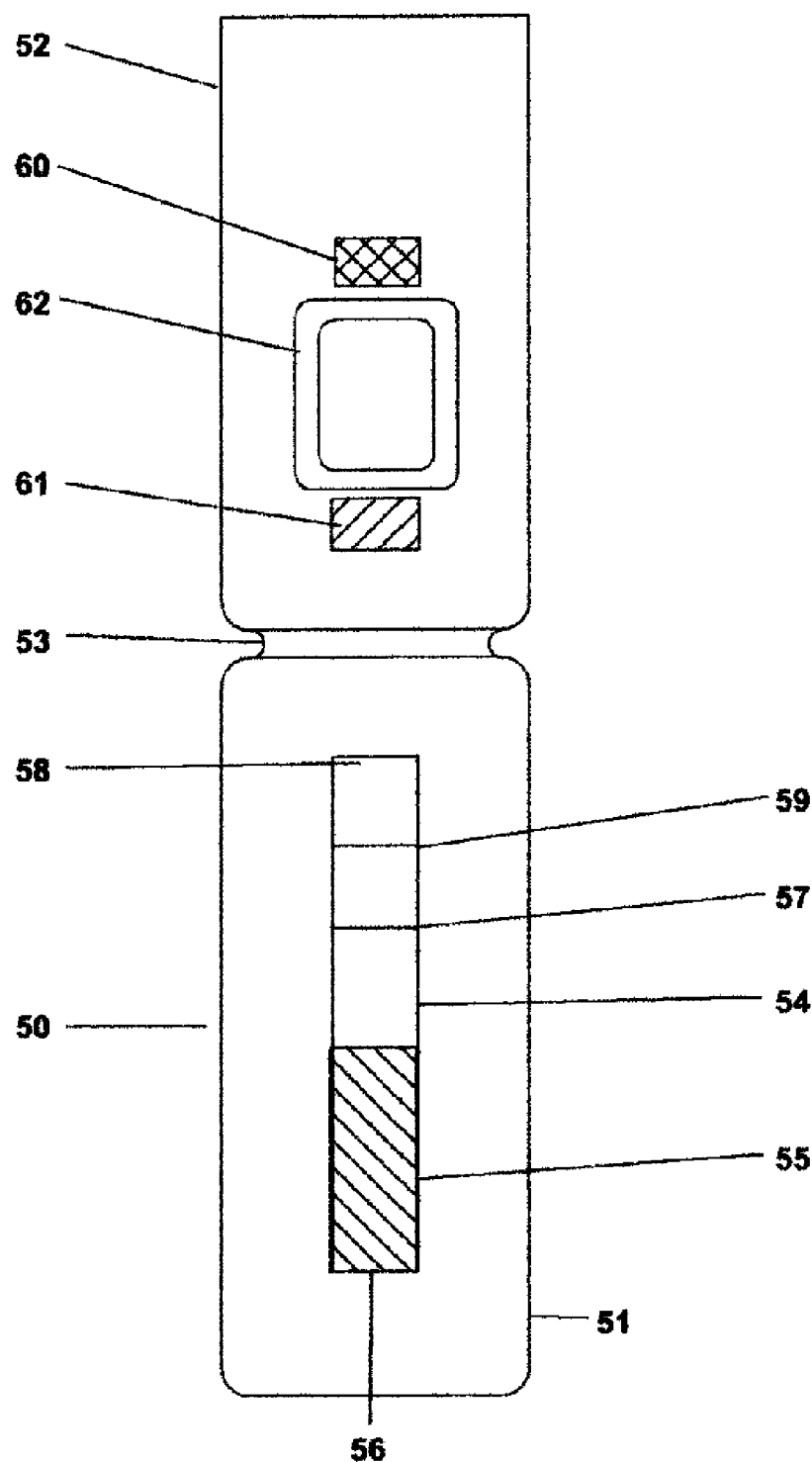
FIG. 6 is a top view of a further embodiment of the invention in a hinged structure.

In FIG. 6, the device (50) comprises a first opposable component (51) and a second opposable component (52) joined by a flexible member or hinge (53). As the description proceeds, the skilled artisan will recognize that the hinge (53), while convenient, is not a necessary element. In fact, components (51) and (52) may be completely separate and subsequently brought together to permit the desired reactions to take place. The first component (51) contains a chromatographic test strip (54) with a sample zone (55) at its proximal end (56). A test zone (57) is placed downstream of the sample pad (55) and contains a fixed unlabeled reactant, for example an antibody to the analyte. Still farther downstream towards the distal end of the chromatographic medium (54) is a control zone (59). The control zone is not essential but serves as an aid permitting the operator to see that the test strip is completely wetted. The second component (52) contains a conjugate pad (60) and a absorbent pad (61). The conjugate pad (60) contains a labeled detection reagent, for example, a labeled antibody to the analyte. When the two opposable components (51, 52) are brought together the labeled detection reagent migrates to the test strip and downstream by capillary action towards the test zone (54), the control zone (57) and toward the absorbent sink (61).

If an antigen analyte is present, the first reaction in this device is the formation of a fixed, unlabeled binder/analyte product in the test zone. The second reaction is between the product and the mobile, labeled detection reagent, for example, a gold labeled antibody to the antigen to form a detectable complex which can be observed and its intensity determined through the window (62).

Features common to all of the devices of this invention described above and of equivalent devices are that the analyte when present reacts on a chromatographic test strip first with a fixed unlabeled reactant to form a fixed product which reacts in a second reaction with a mobile, labeled reactant to form a detectable product on the test strip.

Initially, the labeled detection reactant is in a spatial relationship with the test strip such that they are separated until the fixed product forms on the test strip. Subsequently, the formed product is brought into contact with a labeled, mobile reactant which has moved downstream through the test strip until it contacts and reacts with the fixed product to form a detectable complex.

It is preferred, but not essential, that the device contains an absorbent sink to facilitate the movement of the sample through the strip.

If, for example, the device is intended for the determination of a protein, the test strip will include a test zone with a fixed unlabeled antibody to the protein. The sample containing the protein will move through the test strip until it contacts a fixed, unlabeled first capture antibody to the protein. As a result an analyte/antibody binary product forms. Spaced apart from, but positioned on the device so that it can be moved into contact with the test strip, there is a source of a mobile, labeled second detection antibody, usually termed a detection reagent. After the binary product forms and is fixed on the test strip, the second antibody to the protein is contacted with the test strip upstream of the binary product. It moves towards and reacts with the binary product to form a first antibody/analyte/second antibody detectable ternary complex.

The present invention includes various means for bringing the absorbent sink component and reagent reservoir component, or additional elements of the assay devices of the present invention into contact with the wet chromatographic medium after the analyte has been immobilized in the test zone by reaction with a capture reagent. These means may include gravitationally dropping movable components onto a fixed test strip by turning the entire assay device. In some embodiments, the movable components may be situated within a rotatable outer member, thereby maintaining the test strip in a stationary position, and rotating or turning part of the test device to effect contact or gravitational movement. These means may also include removing a barrier that prevents contact between the components and the test strip; actuating devices such as push-pins or pull-pins or the like outside the housing that press one or more components into contact with the test strip in a sequence determined by the operator; hinge devices to bring two opposable segments into contact; magnetic forces generated by the application of a magnet to the outside of the housing to bring the magnetized components into contact with the test strip; and other variations, all of which are within the scope of the present invention.

The chromatographic media or test strips for use with the present invention is typically a porous membrane. The membrane should be capable of transporting a liquid by capillary forces over a distance. The membrane should also be capable of binding reactants in the test zone, and optionally, in other regions of interest, either by covalent attachment, non-covalent attachment, or physical attachment.

Suitable chromatographic media for use in the present invention include porous media of natural or synthetic fiber, such as nylon, polyester, cellulose-based polymeric substances, sintered structures composed of particulate materials such as glass or various thermoplastic polymers; or cast membrane films, often synthetic, such as nitrocellulose, nylon, polysulfone and the like. The chromatographic media may be assembled as a multi-layered component. The preferred thickness of the medium pore size of the chromatographic medium depends, in part, on the nature of the sample which is to be applied to the media, and the desired rate of fluid flow through the porous media, the test time, and the test sensitivity. Determination of the most preferred pore size for any particular application is within the knowledge of those skilled in the art. Generally, a pore size of between 3 µm and 12 µm is preferred. Preferred commercially available membranes include Purabind™ A-SP, 3 µm, (Whatman International) Millipore Hiflow Plus (Millipore Corporation, Bedford, Mass.); Unisart CN 140(Sartorius AG, Gottingen, Germany) and FF125 (Schleicher & Schuell BioScience, Inc. Keene, N.H.).

The shape of the test strip is not generally limited, although it is preferred that whatever shape is chosen, the test strip itself be substantially planar when in operation. In practice, it is desirable to minimize the size of the test strip, to reduce the volume of sample required for wetting, and to concomitantly reduce the amount of the test strip material, provided that the desired test sensitivity is attained.

The test strip may be one length of the selected material or different lengths arranged in series. The separate lengths may be in end to end configuration, or one may slightly overlap the other. For example the upstream length may be of fiberglass of appropriate pore size to filter particles such as red blood cells out of the sample. The downstream test zone may be of nitrocellulose. Another convenient arrangement is to construct the strip of nitrocellulose with the upstream segment of a pore size to filter particles and the downstream segment having properties adaptable for use as a test zone and a control zone.

The selected reactants such as the detection reagent and the capture reagent may be immobilized and arranged onto the chromatographic medium by methods known to those of skill in the art.

The absorbent sink for use in the present invention is any material that is capable of rapidly absorbing liquid from the test strip. The absorbent material used for any given test is of sufficient volume to absorb as least as much liquid drawn from the test strip by capillary forces in order that the reagent or other material from the reservoir crosses the test zone. Suitable materials include any one of a number of known hydrophilic absorbent powders and paper or cellulose based materials such as nitrocellulose or filter paper.

In some embodiments of the invention, it is not necessary to prepare an absorbent sink to be moved into contact with the test strip. Instead the downstream distal end of the test strip will serve the same purpose. For example, a test strip of chromatographic medium can be prepared which has a volumetric capacity equal to or larger than the sample volume to be placed onto the strip. In operation, the capillary flow of the predetermined volume of sample will leave a dry portion of the test strip at the distal end of the test strip, which itself may later act as an absorbent sink. Provided that the sample flow has proceeded through the test zone (but not to the absorbent sink), the reagent reservoir can then be contacted, in a timely manner, with the chromatographic medium to solubilize the reagent and mobilize it through the test zone due to the additional absorbent capacity at the end of the test strip. In such embodiments where the volumetric capacity is larger than the sample volume to be placed onto the strip, it may be necessary to add further sample volume after contacting the reagent reservoir with the wetted test strip.

The reservoir support material should be a generally chemically inert substance. Chemical interaction between the reservoir support material and the reagent housed thereon is generally undesirable. The reservoir support material must also be capable of discharging the reagent on the wetted test strip when the strip comes into contact with the reagent reservoir. The discharge preferably occurs by solubilization of the labeled reactant and subsequent movement thereof through the strip by capillary action to form the binary product.

The reservoir support material should also be generally non-absorbent. It is preferable that the reservoir support material not absorb the liquid sample from the wetted test strip, as such absorption could interfere with the efficiency of the resolubilization of a conjugate. Absorption of the conjugate into the reservoir support material may interfere with the sensitivity and efficiency of the assay.

The shape and size of the reservoir support are generally not limited, however it is preferable that the surface of the reservoir support upon which the conjugate is housed is substantially planar, to provide an efficient engagement with a substantially planar chromatographic medium when the two elements are moved into contact. Depending on the means chosen for bringing the reagent reservoir into contact with the wetted test strip, in some embodiments it is preferable to choose the reservoir support from a resilient material such as silicon rubber or closed cell foam. In some embodiments, the reagent reservoir may be deposited on an interior edge of the housing of the assay device.

Blocking agents are not essential for use with the labeled reagent of the present invention. The selection of a generally inert and non-absorbent material as the reservoir support renders unnecessary the application of a blocking agent to the reservoir support material, either in a separate deposit step, or as part of the labeled reactant mix. Moreover, in accordance with the present invention the conjugate does not contact the test strip until it has been wetted with the liquid sample. Depending on the nature of the sample, the non-specific binding capacity of the test strip may be saturated by sample components, thereby rendering a blocking agent on the test strip itself unnecessary.

In embodiments of the invention where it is desirable to have reservoirs of more than one type of reagent, it is not essential that each reservoir be housed upon its own reservoir support. In some embodiments of the invention, the test strip-contacting face of the reservoir support may house spatially discrete reservoirs of reagents, which can be contemporaneously or sequentially loaded onto and dried down upon the reagent support material.

The label for use in the present invention can be any direct or indirect label which can be readily detected. Preferably the label is one which is visible in normal light to the naked eye, and does not need any extrinsic aids for detection, such as magnifying devices, optical readers, filters or specialized light sources. Concentration of the labeled reactant into the test zone should give rise to a readily detectable signal.

Labels can include direct labels such as colloidal labels from any one of a large number known to the skilled artisan. For example, dye sols and gold sols, and latex particles. Latex (polymer) particles for use in immunoassays are commercially available. These can be based on a range of synthetic polymers, such as polystyrene, polyvinyltoluene, polystyrene-acrylic acid and polyacrolein. The latex particles can be colored by either incorporating a suitable dye, e.g. anthraquinone, during manufacture, or by coloring the pre-formed particles. Preferred direct labels include metallic or non-metallic colloidal labels. Gold is the preferable metallic colloidal label. Preparation of colloidal gold labels is described in *Immunocytochemical Methods and Protocols, 2$^{nd}$ Edition, L. C. Javois, ed., Humana Press, 1999*. Gold colloidal labels are commercially available either alone or attached to reactants for use in the present invention from Arista Biologicals Inc., Allentown Pa., and British Biocell International, Cardiff UK, among others.

Labels can include indirect labels, in which an additional step or reactant is required for visualization of the label. For example, the use of the enzyme alkaline phosphatase conjugated to a binding partner for the analyte of interest can be followed by development of the detectable color signal by the addition of p-nitrophenylphosphate, a substrate for alkaline phosphatase activity. Indirect labels for use with the present invention include the enzyme alkaline phosphatase and its corresponding substrates, horseradish peroxidase and its corresponding substrates, beta-galactosidase and its corresponding substrates, glucose oxidase and its corresponding substrates.

The support structure upon which the chromatographic medium is disposed can be any suitable inert, generally rigid material. The exact material, shape and dimension of the support structure used in any particular embodiment will depend on a variety of factors known to those of skill in the art, including the means chosen for engaging the chromatographic medium with the reagent reservoir and the absorbent sink. Suitable support structure materials include plastic, glass, paper, metal or foams. A preferred support structure is made from a lightweight plastic material.

The labeled detection reagent can be applied to the reservoir support material in a variety of ways known to those of skill in the art. Various techniques include microsyringes, ink-jet printing, direct printing, manual pipetting, and pens using metered pumps. The labeled reagent is dried onto the reservoir support material using a variety of methods known to those of skill in the art including lyophilization and drying under heat.

The housing for the assay device can be any structure that will protect the inner components of the assay device from physical damage. Preferably the housing is a liquid impervious plastic. In some embodiments of the invention, the housing can be transparent, which may obviate the need for an aperture to view the test zone. The housing may be of integral construction, or it may be comprised of portions to be assembled during manufacture, which preferably are not easily pried apart by the user. In some embodiments of the present invention, one or more interior surfaces of the housing may come into contact with the chromatographic medium. In such embodiments, it is desirable that any irregularities on those surfaces be removed, as they may interfere with the evenness of the flow across the chromatographic medium.

The housing may be provided with sample application means. Preferably, the sample application means are an aperture for sample application. This aperture may take a variety of forms, which are known to those of skill in the art. Such forms include a hole in the housing directly adjacent to the strip, to permit the sample to be pipetted directly onto the strip. In other embodiments, the test strip may extend beyond the housing for ease of sample application directly onto the test strip, as, for example, where a user may contact the test strip with a finger prick drop of blood, serum, or a urine stream. In other embodiments, the test strip may extend from the housing in a recessed zone, for example, a semi-circular recess which corresponds to the shape of a finger, in order that a finger prick of blood may be directly placed onto the test strip by a patient. Optionally, the sample application means may include a sample receiving member which protrudes from the housing, and allows the sample to flow through the sample receiving member through to the chromatographic medium. The sample receiving member may be any suitable porous, bibulous or fibrous material capable of absorbing liquid rapidly, as described, for example, in May et al. U.S. Pat. No. 5,622,871. Further, the sample receiving member may have a cap or other protective device to protect the sample receiving member when it is not in use.

The assay devices of this invention will normally be produced for distribution in test kits. Such kits will comprise at least one assay device packaged in a container sufficiently impervious to the environment to protect the contents from possible degradation and of sufficient strength to protect the contents from physical damage during handling. Other contents of the test kit will vary depending on the intended use. For assays based on blood, the kit may contain an instrument, such as a needle, knife, lance or blade for piercing the finger to obtain a drop of blood. The kit may also contain a small amount of a packaged hygroscopic agent such as calcium chloride to protect the device from moisture. Additionally, the kit may contain package inserts and user information describing the contents and the method of using the device.

The binding assays of the present invention, while not so limited, are especially useful for the detection of any analyte for which there is an available known specific binding partner. These may include any peptide, protein, carbohydrate or glycoprotein for which a specific binding partner exists, either naturally or synthetically. The analyte is often selected from the group consisting of antigens and antibodies thereto, as well as receptors, intermediates, degradation products, and binding substances of these analytes.

The following examples are given by way of illustration only and are not to be considered as limitations of the invention since many apparent variations are possible without departing from the spirit or scope of the invention.

EXAMPLE 1

An elongated rectangular test strip of chromatographic media having the dimensions of 5 mm×60 mm was prepared from a polyester film supported nitrocellulose membrane [Purabind™ A-SP, 3 µm, Whatman International, Maidstone, Kent, UK].

One end of the test strip was selected as the sample application zone. A test zone was prepared approximately 25 mm downstream from the sample application zone of the test strip by pipetting a 1 µl dot containing capture antibodies [anti-alpha hCG goat antibodies, 2 mg/ml, Arista Biologicals Inc., Allentown Pa.] onto the test strip. The strip was then dried for 30 minutes at 37° C.

The support material for the reservoir of labeled reagent was prepared using a block of silicone rubber in the dimensions of 5 mm×5 mm×3 mm. The labeled reagent was a gold-antibody conjugate (OD=5) loaded with anti-beta hCG monoclonal mouse antibodies [Arista Biologicals Inc.]. 1.5 µl of the labeled reagent was pipetted onto one surface of the silicone block and dried onto this surface for 30 minutes at 37° C.

Forty (40) µl of a sample solution consisting of human serum spiked with hCG (Sigma-Aldrich Corporation, St. Louis, Mo.) to a concentration of 50 mIU/ml was applied to the sample application zone of the nitrocellulose membrane. By capillary action, the entire test strip was wetted with the sample solution. The membrane was completely wetted in approximately three minutes. As the volume of sample added was larger than the volumetric capacity of the test strip, a small surplus of liquid was left at the sample application zone.

The silicone rubber block was placed, reagent side facing down, between the test zone and the sample application zone. On the opposite side of the test zone, a spoonful of powder [~50 mg Zeeosperes W610, 3M Corporation] was added at approximately the same time. Within a few seconds the solubilized gold-antibody conjugate moved by capillarity out from under the silicone rubber block, crossing the test zone, and causing an intense red dot to form on the test zone. The red dot was caused by the anti-alpha hCG goat antibodies which had been immobilized in the test zone binding to the hCG in the sample, and that conjugate being further bound by the labeled anti-beta hCG monoclonal mouse antibodies. The excess labeled reagent moved through the test zone and into the absorbent powder.

A control test assay was prepared and run in identical fashion, with the exception that the human serum sample not spiked with hCG. No positive signal was observed in the test zone on the control test strip.

EXAMPLE 2

An elongated rectangular test strip of chromatographic media having the dimensions of 5 mm×60 mm is prepared from a polyester film supported nitrocellulose membrane [Purabind™ A-SP, 3 µm, Whatman International, Maidstone, Kent, UK].

One end of the test strip is selected as the sample application zone. A test zone is prepared approximately 25 mm downstream from the sample application zone of the test strip by pipetting a 1 µl dot containing capture antibodies [anti-alpha hCG goat antibodies, 2 mg/ml, Arista Biologicals Inc., Allentown Pa.] onto the test strip. The strip is then dried for 30 minutes at 37° C.

The support material for the reservoir of labeled reagent is prepared using a block of silicone rubber in the dimensions of 5 mm×5 mm×3 mm. The labeled reagent is gold-antibody conjugate (OD=5) loaded with anti-beta hCG monoclonal mouse antibodies [Arista Biologicals Inc.]. 1.5 µl of the labeled reagent is pipetted onto one surface of the silicone block and dried onto this surface for 30 minutes at 37° C. The device is assembled inside an outer housing, so that the test zone is observable through a viewing window, and the sample application zone is available to be contacted by the sample.

Forty (40) µl of a sample solution consisting of human serum spiked with hCG (Sigma-Aldrich Corporation, St. Louis, Mo.) to a concentration of 50 mIU/ml is applied to the sample application zone of the nitrocellulose membrane. By capillary action, the entire test strip is wetted with the sample solution. The membrane is completely wetted in approximately 3 minutes. As the volume of sample added is larger than the volumetric capacity of the test strip, a small surplus of liquid is left at the sample application zone.

The test device is then turned upside down, causing the reagent reservoir to contact the now wetted membrane, and thereby solubilizing the gold-antibody conjugate. At the same time, the powder makes contact with the wetted membrane, which permits it to absorb additional sample volume. The solubilized gold-antibody conjugate moves by capillarity across the test zone, and causing an intense red dot to form on the test zone. The red dot was caused by the anti-alpha hCG goat antibodies which had been immobilized in the test zone binding to the hCG in the sample, and that conjugate being further bound to the now immobilized hCG. The excess labeled reagent moved through the test zone and into the absorbent powder.

A control test assay is prepared and run in identical fashion, with the exception that the human serum sample not spiked with hCG. No positive signal is observed in the test zone on the control test strip.

While certain embodiments of the present invention have been described herein, it should be understood that the invention herein extends to all modifications and variations as will be apparent to a reader skilled in the art in light of the foregoing descriptions of the preferred embodiments thereof.

What is claimed is:

1. A chromatographic assay device for the analysis of an analyte in a liquid sample, said device comprising:
   a) chromatographic medium having a proximal sample application zone and a distal test zone, in which the test zone contains a first ligand capable of binding with the analyte to form an analyte-ligand complex;
   b) a spatially distinct reservoir containing a labeled reagent capable of binding to the analyte-ligand complex;
   c) an absorbent sink which is positioned to be capable of drawing the contents of the spatially distinct reservoir through the test zone; and
   d) means for contacting the spatially distinct reservoir with the chromatographic medium so that the labeled reagent migrates from the reservoir to the absorbent sink, and thereby through the test zone to determine the presence or absence of the analyte.

2. The assay device of claim 1 wherein the labeled reagent is labeled with a colloidal particle.

3. The assay device of claim 1 wherein the labeled reagent is labeled with gold.

4. The assay device of claim 1 wherein the first ligand is an unlabelled capture antibody.

5. The assay device of claim 4 wherein the labeled reagent is a detection antibody.

6. A chromatographic assay device for the analysis of at least one analyte in a liquid sample, said device comprising:
   a) a chromatographic medium having a proximal sample application zone and a distal test zone, in which the test zone contains a first ligand capable of binding with the analyte to form an analyte-ligand complex;
   b) at least one spatially distinct reservoir containing a labeled reagent capable of binding to the analyte-ligand complex;
   c) at least one absorbent sink which is positioned to be capable of drawing the contents of the at least one spatially distinct reservoir through the test zone; and
   d) means for contacting the spatially distinct reservoir with the chromatographic medium so that the labeled reagent migrates from the reservoir to the absorbent sink, and thereby through the test zone to determine the presence or absence of the analyte.

7. The assay device of claim 6 wherein the labeled reagent is labeled with a colloidal particle.

8. The assay device of claim 6 wherein the labeled reagent is labeled with gold.

9. The assay device of claim 6 wherein the first ligand is an unlabelled capture antibody.

10. The assay device of claim 9 wherein the labeled reagent is a detection antibody.

11. A method for determining the presence or absence of at least one analyte in a liquid sample comprising the steps of:
    a) providing a chromatographic assay device comprising a chromatographic medium having a test zone containing at least one immobilized ligand capable of binding the analyte and thereby forming a ligand-analyte pair, and further comprising at least one spatially distinct reservoir containing a labeled reagent capable of binding to the ligand-analyte pair, and further comprising an absorbent sink;
    b) contacting the liquid sample with a proximal end of the chromatographic medium such that the sample is chromatographically transported to a distal test zone, and thereby form a ligand-analyte pair;
    c) contacting the labeled reagent and the absorbent sink with the chromatographic medium to chromatographically draw the labeled reagent through the test zone; and
    d) detecting bound labeled reagent at the test zone to determine the presence or absence of at least one analyte in the liquid sample.

12. The method of claim 11 in which the liquid sample is selected from the group consisting of blood, urine, and saliva.

13. The method of claim 11 in which the liquid sample is blood.

14. An analytical test device suitable for determining the presence, absence, or quantity of an analyte in a liquid sample said device comprising a housing which contains:
    (a) a first component which is a chromatographic test strip through which the sample flows by capillary action from a sample application zone to contact a downstream test zone on the test strip, said downstream test zone containing an unlabelled immobile first reactant which reacts with the analyte if present to form an unlabelled reactant/analyte product;
    (b) a second component separated from the first component and carrying a second, mobilizable, labeled reactant which is so placed on as to be moved into contact with the unlabelled reactant/analyte product to form a detectable unlabelled reactant/analyte/labeled reactant complex;
    said first reactant and said second reactant being initially separate but in a spatial relationship such that they can be brought together after formation of the unlabelled reactant/analyte product to permit the reaction which forms the detectable unlabelled reactant/analyte/unlabelled reactant complex.

15. A device as in claim 14 further comprising an absorbent sink provided downstream of said test zone.

16. A device as in claim 14 wherein the label is a colloidal particle label.

17. A device as in claim 14 wherein the label is gold.

18. A device as in claim 14 wherein the first reactant is an unlabelled capture antibody and the analyte is an antigen which the antibody binds to form a reaction product.

19. A device as in claim 18 wherein the second reactant is a labeled detection antibody which forms a complex with the reaction product.

20. A device as in claim 19 wherein the label is gold.

21. A method for determining the presence, absence or quantity of at least one analyte in a liquid sample comprising the steps of:
    a) providing an assay device comprising a housing which contains
       i. a first component which is a chromatographic test strip through which the sample flows by capillary action from a sample application zone to contact a downstream test zone on the test strip, said downstream test zone containing an unlabelled immobile first reactant which reacts with the analyte if present to form an unlabelled reactant/analyte product;
       ii. a second component separated from the first component and carrying a second, mobilizable, labeled reactant which is so placed on as to be moved into contact with the unlabelled reactant/analyte product to form a detectable unlabelled reactant/analyte/labeled reactant complex;
    said first reactant and said second reactant being initially separate but in a spatial relationship such that they can be brought together after formation of the unlabelled reactant/analyte product to permit the reaction which forms the detectable unlabelled reactant/analyte/labelled reactant complex;

b) contacting the sample application zone with the liquid sample such that the analyte moves to the test zone by capillary action to form a reaction product;

c) contacting the labeled reagent with the reaction product to form a detectable reaction complex; and d) detecting the reaction complex to determine the presence, absence or quantity of said at least one analyte in the liquid sample.

22. The method of claim 21 in which the assay device includes an absorbent sink on one of the components to facilitate the capillary movement of the liquid sample.

23. The method of claim 21 in which the analyte is human chorionic gonadotropin.

24. The method of claim 21 in which the liquid sample is selected from the group consisting of urine, blood, and saliva.

25. The method of claim 21 in which the liquid sample is human blood.

26. A test kit containing the device of claim 1 in packaged combination with instructions for use.

27. A test kit containing the device of claim 14 in packaged combination with instructions for use.

* * * * *